United States Patent [19]

Tessier et al.

[11] Patent Number: 4,801,717
[45] Date of Patent: * Jan. 31, 1989

[54] HYDROXYLAMINE DERIVATIVE OF 5-NITRO-8-HYDROXY QUINOLINE

[75] Inventors: Jean Tessier, Vincennes; Pierre Girault, Paris; Jean-Jacques Herve, Aubagne; Charles-Jacques Van Assche, Marseille, all of France

[73] Assignee: Roussel Uclaf, Paris, France

[ * ] Notice: The portion of the term of this patent subsequent to Sep. 18, 2001 has been disclaimed.

[21] Appl. No.: 877,884

[22] Filed: Jun. 24, 1986

Related U.S. Application Data

[62] Division of Ser. No. 582,320, Feb. 22, 1984.

[30] Foreign Application Priority Data

Feb. 23, 1983 [FR] France ................. 83 02916

[51] Int. Cl.$^4$ ............................. C07D 215/24
[52] U.S. Cl. .................... 546/177; 546/176; 564/300
[58] Field of Search ............. 546/176, 177; 564/300

[56] References Cited

U.S. PATENT DOCUMENTS 3,118,933 1/1964 Goldberg et al. ............ 564/300
4,472,194 9/1984 van Asshe et al. .......... 564/300 X

FOREIGN PATENT DOCUMENTS 169446 9/1985 Japan ..................... 564/300

Primary Examiner—David B. Springer
Attorney, Agent, or Firm—Bierman and Muserlian

[57] ABSTRACT

Novel hydroxylamino derivatives of the formula

Ar—ONH$_2$    I wherein Ar is selected from the group consisting of mono- and polycyclic aromatics and hetero-aromatics, both optionally substituted with at least one member of the group consisting of —OH, halogen, —NO$_2$, —CN,

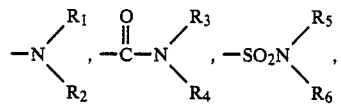

—R$_7$, —OR$_8$,

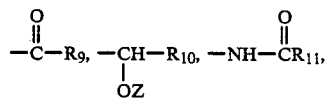

—SO$_2$R$_{12}$, —SO$_3$R$_{13}$, —COOR$_{14}$, aryl of 6 to 14 carbon atoms, —OR$_{16}$, —CH$_2$—CN and —CH$_2$SO$_2$—R$_{15}$, R$_1$, R$_2$, R$_3$, R$_4$, R$_5$ and R$_6$ are individually selected from the group consisting of hydrogen and alkyl of 1 to 8 carbon atoms, R$_7$ and R$_8$ are optionally unsaturated alkyl of 1 to 8 carbon atoms optionally substituted with at least one member of the group consisting of halogen and cyano, R$_9$, R$_{10}$, R$_{11}$, R$_{12}$ and R$_{13}$ are alkyl of 1 to 8 carbon atoms, Z is selected from the group consisting of hydrogen, optionally unsaturated alkyl of 1 to 8 carbon atoms and acyl of an organic carboxylic acid of 2 to 18 carbon atoms, R$_{14}$ is selected from the group consisting of hydrogen and alkyl of 1 to 8 carbon atoms, R$_{15}$ is selected from the group consisting of alkyl of 1 to 8 carbon atoms and aryl of 6 to 14 carbon atoms optionally substituted with an alkyl of 1 to 8 carbon atoms, R$_{16}$ is aryl of 6 to 14 carbon atoms optionally substituted with a member of the group consisting of alkyl of 1 to 8 carbon atoms, halogen and —NO$_2$, the substituents of Ar being able to form rings containing at least one heteroatom selected from the group consisting of oxygen, nitrogen and sulfur and their non-toxic agriculturally acceptable acid addition salts with the proviso Ar is not phenyl nor phenyl with one methyl in the 2,3 or 4 position, a nitro in the 2- or 4-position, a chlorine in the 3- or 4-position, a bromine in the 4-position or a —CF$_3$ in the 4-position nor 2,4-dinitrophenyl nor 2-nitro-4-trifluoromethylphenyl nor 2,6-dinitrophenyl nor 2,4,6-trinitrophenyl nor 2,4-dinitro-6-trifluoromethylphenyl useful for increasing vegetation growth and increasing crop yields and their preparation.

1 Claim, No Drawings

HYDROXYLAMINE DERIVATIVE OF 5-NITRO-8-HYDROXY QUINOLINE

This is a division of Ser. No. 582,320, filed Feb. 22, 1984.

STATE OF THE ART

The J. Med. Chem., Vol. 10, No. 3 (1967), p. 512 describes nine aryloxycarbamates prepared by reacting a chloroformate ester with the corresponding aryloxyamines, Swenson et al [J. Org. Chem., Vol. 39, No. 22 (1973), p. 3956-3758] describe the Lossen rearrangement of nitrophenylbenzhydroxamates, Endo et al in Synthesis, No. 6 (1980), p. 461–463 describe O-arylhydroxylamines optionally substituted in the 3- or 4-position with methyl or chlorine. Sheradsky et al describe in Tetrahedron, Vol. 28, No. 14 (1972), p. 3833–3843 O-(nitroaryl)hydroxylamines as intermediates. French Pat. No. 1,430,927 describes pesticidal esters. Copending, commonly assigned U.S. patent application Ser. No. 462,084 filed Jan. 28, 1983 describes several O-arylhydroxylamines for increasing the growth of vegetables.

OBJECTS OF THE INVENTION

It is an object of the invention to provide the novel hydroxylamines of formula I and their non-toxic, agriculturally acceptable acid addition salts and their preparation.

It is another object of the invention to provide novel compositions for increasing the growth of vegetables and a method of increasing vegetable growth.

These and other objects and advantages of the invention will become obvious from the following detailed description.

THE INVENTION

The novel compounds of the invention are selected from the group consisting of hydroxylamino derivatives of the formula $$Ar-ONH_2 \qquad I$$

wherein Ar is selected from the group consisting of mono- and polycyclic aromatics and hetero-aromatics, both optionally substituted with at least one member of the group consisting of —OH, halogen, —NO$_2$, —CN,

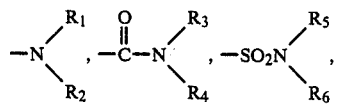

—R$_7$, —OR$_8$,

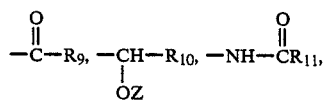

—SO$_2$R$_{12}$, —SO$_3$R$_{13}$, —COOR$_{14}$, aryl of 6 to 14 carbon atoms, —OR$_{16}$, —CH$_2$—CN and —CH$_2$SO$_2$—R$_{15}$, R$_1$, R$_2$, R$_3$, R$_4$, R$_5$ and R$_6$ are individually selected from the group consisting of hydrogen and alkyl of 1 to 8 carbon atoms, R$_7$ and R$_8$ are optionally unsaturated alkyl of 1 to 8 carbon atoms optionally substituted with at least one member of the group consisting of halogen and cyano, R$_9$, R$_{10}$, R$_{11}$, R$_{12}$ and R$_{13}$ are alkyl of 1 to 8 carbon atoms, Z is selected from the group consisting of hydrogen, optionally unsaturated alkyl of 1 to 8 carbon atoms and acyl of an organic carboxylic acid of 2 to 18 carbon atoms, R$_{14}$ is selected from the group consisting of hydrogen and alkyl of 1 to 8 carbon atoms, R$_{15}$ is selected from the group consisting of alkyl of 1 to 8 carbon atoms and aryl of 6 to 14 carbon atoms optionally substituted with an alkyl of 1 to 8 carbon atoms, R$_{16}$ is aryl of 6 to 14 carbon atoms optionally substituted with a member of the group consisting of alkyl of 1 to 8 carbon atoms, halogen and —NO$_2$, the substituents of Ar being able to form rings containing at least one heteroatom selected from the group consisting of oxygen, nitrogen and sulfur and their non-toxic agriculturally acceptable acid addition salts with the proviso that Ar is not phenyl nor phenyl with one methyl in the 2, 3 or 4 position, a nitro in the 2 or 4-position, a chlorine in the 3- or 4-position, a bromine in the 4-position or a —CF$_3$ in the 4-position nor 2,4-dinitrophenyl nor 2-nitro-4-trifluoromethylphenyl nor 2,6-dinitrophenyl nor 2,4,6-trinitrophenyl nor 2,4-dinitro-6-trifluoromethylphenyl, When Ar is aromatic, it is preferably selected from the group consisting of phenyl, napthyl and anthracenyl radicals. When Ar is a hetero-aromatic radical, it is preferably a pyridyl, quinolyl, benzothiazolyl or oxazolyl radical. When Ar is substituted by a halogen, the halogen is preferably fluorine, chlorine or bromine.

When R$_1$, R$_2$, R$_3$, R$_4$, R$_5$ or R$_6$ is an alkyl, it is preferably methyl, ethyl, n-propyl or n-butyl. When R$_7$, R$_8$, R$_9$, R$_{10}$, R$_{11}$, R$_{12}$, R$_{13}$ or R$_{14}$ is an alkyl, it is preferably methyl, ethyl, n-propyl, isopropyl, n-butyl, isobutyl or tert.-butyl. When R$_7$ or R$_8$ is an alkyl substituted by at least one halogen, it is preferably —CF$_3$, —CHCl$_2$, —CCl$_3$, —OCF$_3$, —OCHCl$_2$ or —OCCl$_3$. When R$_7$ or R$_8$ is an unsaturated alkyl, it is preferably vinyl, allyl or propargyl.

When Z is a saturated alkyl, it is preferably methyl, ethyl, n-propyl, isopropyl or tert.-butyl. When Z is an unsaturated alkyl, it is preferably vinyl, allyl or propargyl. When Z is an acyl, it is preferably acetyloxy or propionyloxy.

When Ar is substituted with an aryl, it is preferably an aryl substituted by a phenyl.

When R$_{15}$ is an alkyl, it is preferably methyl, ethyl, n-propyl or n-butyl and when R$_{15}$ is an aryl, it is preferably phenyl or p-tolyl. R$_{16}$ is an aryl radical, preferably phenyl, and when R$_{16}$ is substituted, the substituent is preferably methyl, ethyl, n-propyl, isopropyl, chlorine, bromine or iodine or nitro.

When Ar is an aromatic or hetero-aromatic substituted by other substituents forming rings with each other, they are preferably selected from the group consisting of

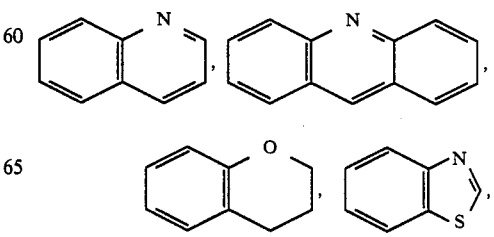

-continued

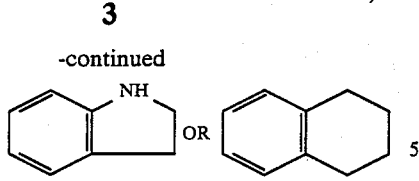

Examples of suitable non-toxic, agriculturaly acceptable acids to form the addition salts are inorganic acids such as hydrochloric acid, hydrobromic acid, sulfuric acid, nitric acid and phosphoric acid and organic acids such as acetic acid, trifluoroacetic acid.

Among the preferred compounds of the invention are those of formula I wherein Ar is phenyl substituted with at least one of the above substituents, especially when at least one is nitro and especially when one is a p-chlorine, and their non-toxic, pharmaceutically acceptable acid addition salts. The preferred compounds of formula I include those wherein Ar is 2-nitro-4-chlorophenyl, 4-nitro-3-alkoxy-phenyl of 1 to 8 alkoxy carbon atoms, especially methoxy or ethoxy and 4-nitro-2-alkyl-phenyl of 1 to 8 alkyl carbon atoms, especially methyl or ethyl.

Other preferred compounds of formula I are those wherein Ar is

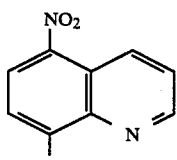

optionally substituted with at least one of the above substituents or

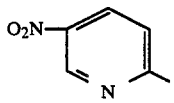

and their non-toxic, agriculturally acceptable acid addition salts.

Examples of specific preferred compounds of formula I are
0-(2-methyl-4-nitrophenyl)-hydroxylamine, 0-(4-nitro-3-methoxyphenyl)-hydroxylamine,
0-(5-nitro-8-quinolyl)-hydroxylamine,
0-(2-chloro-4-nitrophenyl)-hydroxylamine,
0-(2-nitro-4-chlorophenyl)-hydroxylamine,
0-(2,4-dichlorophenyl)-hydroxylamine,
0-(4-nitro-2-trifluoromethylphenyl)-hydroxylamine,
0-[2-(1RS-hydroxyethyl)-4-nitrophenyl]-hydroxylamine,
0-(4-cyanophenyl)-hydroxylamine,
0-[3-(propyn-2-yloxy)-4-nitrophenyl]-hydroxylamine,
0-(3,4-dichlorophenyl)-hydroxylamine and their non-toxic, agriculturally acceptable acid addition salts.

Additional preferred compounds are those of the formula

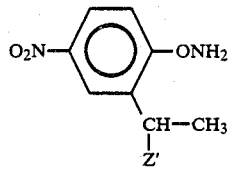

wherein Z' is an acyloxy containing up to 8 carbon atoms or fluorine, chlorine or bromine,

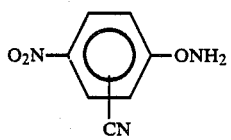

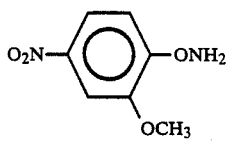

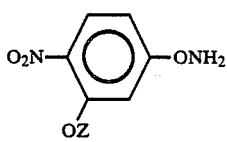

wherein Z is selected from the group

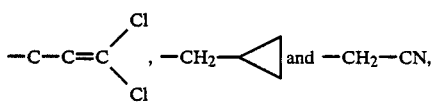

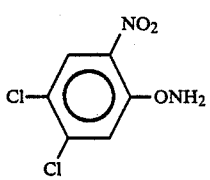

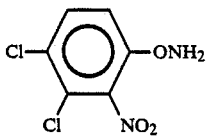

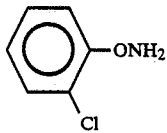

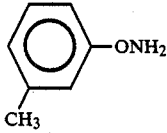

-continued

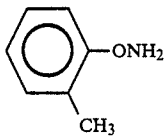

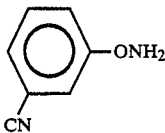

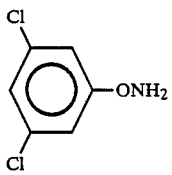

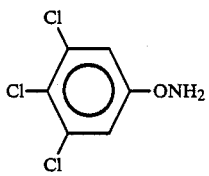

and their non-toxic, pharmaceutically acceptable acid addition salts.

The novel process of the invention for the preparation of the compounds of formula I comprises reacting a compound of the formula

   II wherein Ar has the above definition and Hal is a halogen with a compound of the formula

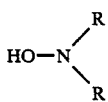   III wherein the Rs are hydrogen or together with the nitrogen atom form phthalimido to obtain a compound of the formula

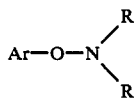   IV which is a compound of formula I when the Rs are hydrogen and when Rs are not hydrogen, reacting the latter with hydrazine to obtain the corresponding compound of formula I and optionally salifying the latter.

In a preferred mode of the process, the Hal of the compound of formula II is fluorine or bromine and the Rs of formula III are hydrogen or hydroxylamine hydrochloride may be reacted with the compound of formula II in solution in an alcohol or aqueous alcohol in the presence of a strong base such as sodium jydroxide or potassium hydroxide or an alkali metal alcoholate. If the compound of formula III is a phtalimido derivative, it is first reacted with a strong base such as sodium hydride or potassium hydride and then with a compound of formula II in an organic solvent such as acetonitrile in the presence of a tertiary base such as pyridine or triethylamine. The salification may be effected in usual organic solvents such as alcohols or ethers or mixtures thereof.

In a modification of the process of the invention, a compound of the formula

   V wherein Ar has the above definition is reacted with a compound of the formula

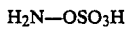   VI to obtain the corresponding compound of formula I and optionally salifying the latter.

The compositions of the invention for increasing the growth rate of vegetables are comprised of vegetable growth increasing amount of at least one compound of formula I and their non-toxic, argiculturally acceptable acid addition salts and a carrier. The compositions may be in the form of powders, granules, suspensions, emulsions and solutions.

Examples of suitable carriers are anionic, non-ionic or cationic surface active agents and vehicles in liquid form such as water, alcohol, hydrocarbons, other organic solvents and animal, vegetable or mineral oils or a powder such as talc, clay, silicates and kieselguhr.

The solid compositions may be in the form of wettable powders, granules or powders for powdering and may be formed by admixing the active compound with an inert solid or by impregnating a solid support with a solution of the active compound and evaporating the solvent.

The compositions may contain 10 to 80%, preferably 10 to 50%, by weight of the active ingredients and may also contain other additional compounds which have an effect on the growth of plants.

The compositions of the invention are useful for improving the physiological state of cultivated vegetables and increasing the weight of harvests. For example, an increase in the weight of harvests may be obtained for roots, pods, fruits and leaves and the compositions may be used on soya, wheat, barley, oats, cotton, beans, tomatoes, onions, potatoes, lettuces, Rosaceae, Compositae, etc. and, more particularly, for plants said to be in $C_3$ or plants for which the first product formed during photosynthesis is a molecule with three carbon atoms. The compositions have the effect of diminishing the inhibition by oxygen of photosynthesis.

Examples of preferred compositions are those containing as the active ingredient at least one compound selected from the group consisting of
0-(2-methyl-4-nitrophenyl)-hydroxylamine,
0-(4-nitro-3-methoxyphenyl)-hydroxylamine,
0-(5-nitro-8-quinolyl)-hydroxylamine,
0-(2-chloro-4-nitrophenyl)-hydroxylamine,
0-(2-nitro-4-chlorophenyl)-hydroxylamine,
0-(2,4-dichlorophenyl)-hydroxylamine,
0-(4-nitro-2-trifluoromethylphenyl)-hydroxylamine,
0-[2-(1RS-hydroxyethyl)-4-nitrophenyl]-hydroxylamine,
0-(3,4-dichlorophenyl)-hydroxylamine,
0-(4-cyanophenyl)-hydroxylamine,
0-[3-(propyn-2-yloxy)-4-nitrophenyl]-hydroxylamine
    and their non-toxic, agriculturally acceptable acid addition salts.

The novel method of the invention for increasing crop yields of vegetables comprises applying to the growing vegetables an amount of at least one compound of formula I and their non-toxic, agriculturally acceptable acid addition salts sufficient to increase the yield of vegetables. The amount will vary depending on the vegetable treated, the nature of the soil, atmospheric conditions and the stage of growth but may vary between 20 to 500 g/ha, preferably between 40 and 120 g/ha.

In the following examples there are described several preferred embodiments to illustrate the invention. However, it should be understood that the invention is not intended to be limited to the specific embodiments.

EXAMPLE 1

0-(2-methyl-4-nitro-phenyl)-hydroxylamine

STEP A: 2-fluoro-5-nitro-toluene 30 g of 2-fluoro-toluene were added at −15° C. over two hours to 33 ml of nitric acid and the mixture was stirred at −15° C. for one hour and was then allowed to rise to 20° C. The reaction mixture was poured into ice and was extracted with ether. The organic phase was washed with water, dried and evaporated to dryness. The residue was rectified to obtain 34.4 g of 2-fluoro-5-nitro-toluene with a boiling point of 100°-101° C. at 10 to 11 mm Hg.

STEP B: 0-(2-methyl-4-nitro-phenyl)-hydroxylamine 22 ml of 400 g of sodium hydroxide per liter were added over 15 minutes at 0° C. to a mixture of 8.35 g of hydroxylamine hydrochloride, 84 ml of water, 15.5 g of the product of Step A and 84 ml of ethanol and the mixture was allowed to return to 20° C. The mixture was stirred at 20° C. for 17 hours and was poured into water. The mixture was extracted with methylene chloride and the organic phase was washed with water, dried and evaporated to dryness. The residue was chromatographed over silica gel and eluted with methylene chloride to obtain 1.1 g of 0-(2-methyl-4-nitro-phenyl)-hydroxylamine melting at 118° C.

EXAMPLE 2

0-(4-nitro-3-methoxy-phenyl)-hydroxylamine

STEP A: 2-nitro-5-fluoro-anisole

A mixture of 32 ml of nitric acid and 95 ml of acetic acid anhydride was added dropwise with stirring at 0° to −5° C. to a solution of 12.6 g of 3-fluoro-anisole in 100 ml of acetic acid anhydride and the mixture was stirred at 0° to 5° C. for one hour. The reaction was poured over ice and was vacuum filtered. The recovered precipitate was dried to obtain 6.77 g of 2-nitro-5-fluoro-anisole with a melting point <50° C.

STEP B: O-(4-nitro-3-methoxy-phenyl)-hydroxylamine 13 ml of a solution of 10N sodium hydroxide were added over 15 minutes at 0° C. to a mixture of 10 g of 2-nitro-5-fluoroanisole, 38 ml of ethanol, 38 ml of water and 4.88 g of hydroxylamine hydrochloride and the temperature was then allowed to rise to 20° to 25° C. The mixture was stirred at room temperature for 6 hours and was vacuum filtered. The product was dried and crystallized from methanol. The mixture was vacuum filtered and the product was dried to obtain 5.85 g of 0-(4-nitro-3-methoxy-phenyl)hydroxylamine melting at 106°-107° C.

EXAMPLE 3

0-(2-chloro-4-nitro-phenyl)-hydroxylamine

STEP A: 3-chloro-4-fluoro-nitrobenzene 50 g of 3,4-dichloro-nitro benzene were added to a mixture of 120 ml of dimethylsulfoxide, 80 ml of benzene and 35 g of potassium fluoride and the mixture was stirred at 180°-185° C. for two hours. The water vapor was entrained and the distillate was extracted with isopropyl ether. The combined organic phases were dried and distilled at 40° C. under a pressure of 3 to 4 mm Hg. The residue was rectified at a pressure of 15 mm Hg to obtain 29 g of 3-chloro-4-fluoro-nitrobenzene melting at 41° to 43° C.

STEP B: 0-(2-chloro-4-nitro-phenyl)-hydroxylamine

A solution of 8.5 g of hydroxylamine hydrochloride in 85 ml of water was added at 5° C. over 5 minutes to a solution of 17.5 g of the product of Step A in 170 ml of ethanol and then 22 ml of 10N sodium hydroxide solution were added thereto. The mixture was stirred at 20° C. for eight hours and was then added to 100 ml of water. The suspension was vacuum filtered and the precipitate was washed with water and dried under reduced pressure. The 9 g of product were crystallized from methanol to obtain 7.6 g of 0-(2-chloro-4-nitro-phenyl)-hydroxylamine melting at 125°-126° C.

EXAMPLE 4

0-(2-nitro-4-chloro-phenyl)-hydroxylamine

STEP A: 2-fluoro-5-chloro-nitrobenzene

A mixture of 120 ml of dimethylsulfoxide, 80 ml of benzene, 35 g of potassium fluoride and 50 g of 2,5-dichloronitrobenzene was heated with stirring to 140° C. and was then heated at 180°-185° C. for three hours and then cooled. The water vapor was entrained and the distillate was extracted with isopropyl ether. The combined organic phases were dried and distilled at 40° C. under reduced pressure and were rectified at 14 mm Hg to obtain 10.1 g of 2-fluoro-5-chloro-nitrobenzene with a refractive index of $n_D^{20} = 1.5558$.

STEP B: 0-(2-nitro-4-chloro-phenyl)-hydroxylamine

A solution of 4.4 g of hydroxylamine hydrochloride in 45 ml of water was added with stirring at 5° C. to a solution of 8.7 g of the product of Step A in 85 ml of ethanol and after the addition of 11 ml of 10N sodium hydroxide solution thereto, the mixture was stirred at 20° C. for six hours. 45 ml of water were added and the mixture was vacuum filtered. The precipitate was washed with water and extracted with methylene chloride. The combined organic phases were washed with water, dried and evaporated to dryness at 40° C. under reduced pressure of 3–4 mm Hg to obtain 2.1 g of 0-(2-nitro-4-chloro-phenyl)-hydroxylamine melting at 125°-126° C.

EXAMPLE 5

0-(5-nitro-8-quinolyl)-hydroxylamine

STEP A: 5-nitro-8-fluoro-quinoline 15 ml of nitric acid were added with stirring at −5° C. to 30 ml of concentrated sulfuric acid and then 16 g of 8-fluoroquinoline were added thereto with stirring over 30 minutes at −5° to 0° C. The mixture was stirred at 0° C. for three hours and was then allowed to return to room temperature. The mixture was stirred at room temperature for two hours and was then poured into a mixture of water and ice. The mixture was vacuum filtered and the product was suspended in water. The mixture was made alkaline by addition of 10% sodium carbonate solution and was extracted with methylene chloride. The organic phase was dried and evaporated to dryness under reduced pressure to obtain 12 g of 5-nitro-8-fluoro-quinoline melting at 132°–133° C.

STEP B: 0-(5-nitro-8-quinolyl)-hydroxylamine

A mixture of 9.6 g of the product of Step A, 300 ml of methanol and 4.4 g of hydroxylamine hydrochloride was heated to 40° C. with stirring and was then cooled to 5° C. 11 ml of 10N sodium hydroxide solution were added thereto at 5° to 10° C. over 30 minutes and the mixture was stirred at 20° C. for six hours and was vacuum filtered. The precipitate was extracted with methylene chloride and the combined organic phases were dried and distilled to dryness under reduced pressure. The residue was added to 15 ml of methylene chloride to obtain 1.6 g of 0-(5-nitro-8-quinolyl)-hydroxylamine melting at 228°–230° C.

EXAMPLE 6

0-(2-nitro-4-carboxy-phenyl)-hydroxylamine 150 ml of nitric acid with a density of 1.42 were added at 0° C. to 300 ml of concentrated sulfuric acid and 50 g of p-fluoro-benzoic acid were added thereto at 0° C. over 30 minutes. The mixture was stirred at 0° C. for one hour and the temperature was allowed to rise to 20° C. The mixture was stirred at 20° C. for 16 hours and was poured over ice. The mixture was vacuum filtered and the product was washed and dried to obtain 47.6 g of 3-nitro-4-fluoro-benzoic acid melting at 123°–124° C. The said product was reacted as in Step B of Example 1 to obtain 0-(2-nitro-4-carboxy-phenyl)-hydroxylamine melting at 215° C.

EXAMPLE 7

0-(4-nitro-2-bromo-phenyl)-hydroxylamine 28.2 g of p-fluoro-nitrobenzene were added to 20° C. to 10.4 ml of bromine and then 20 ml of water followed by 180 ml of concentrated sulfuric acid were added thereto at 0° C. 34 g of silver sulfate were added to the mixture and the temperature was allowed to rise to 20°–25° C. and the mixture was stirred for 16 hours and was poured into water. The mixture was filtered and the filter was washed with water and methylene chloride. The filtrate was extracted with methylene chloride and the organic phase was washed with water, dried over magnesium sulfate, filtered and evaporated to dryness under reduced pressure. The residue was dissolved in isopropyl ether and crystallized therefrom. The mixture was filtered and the product was washed to obtain 8.2 g of 3-bromo-4-fluoro-nitrobenzene melting at 59° C. Using the procedure of Example 1, the latter was reacted to obtain 0-(4-nitro-2-bromo-phenyl)-hydroxylamine melting at 122° C.

EXAMPLE 8

0-benzothiazolyl-hydroxylamine

Using the procedure of Example 1, 2-fluoro-benzothiazole was reacted to obtain 0-benzothiazolyl-hydroxylamine melting at 185°–186° C.

EXAMPLE 9

0-(4-nitro-3-methyl-phenyl)-hydroxylamine 3-fluoro-toluene was reacted to obtain 2-methyl-4-fluoro-nitrobenzen which was then reacted as in Example 1 to obtain 0-(4-nitro-3-methyl-phenyl)-hydroxylamine melting at 100° C.

EXAMPLE 10

0-(4-nitro-3-bromo-phenyl)-hydroxylamine 3-bromo-fluoro-benzene was reacted to obtain 2-bromo-4-fluoro-nitrobenzene melting at 42° C. which was reacted as in Example 1 to obtain 0-(4-nitro-3-bromo-phenyl)-hydroxylamine melting at 95° C.

EXAMPLE 11

0-(4-nitro-2-fluoro-phenyl)-hydroxylamine 1,2-difluoro-benzene was reacted to obtain 3,4-difluoronitrobenzene with a boiling point of 80° C. at 10 mm Hg which was reacted as in Example 1 to obtain 0-(4-nitro-2-fluoro-phenyl)-hydroxylamine melting at 125° C.

EXAMPLE 12

0-(4-nitro-3-ethoxycarbonyl-phenyl)-hydroxylamine 3-fluoro-benzoic acid was reacted to form 3-fluoro-6-nitrobenzoic acid melting at 139° C. which was then reacted with ethanol to obtain ethyl 3-fluoro-6-nitro-benzoate melting at <50° C. The latter was reacted as in Example 1 to obtain 0-(4-nitro-3-ethoxycarbonyl-phenyl)-hydroxylamine melting at 92° C.

EXAMPLE 13

0-(2,4-dinitro-5-methyl-phenyl)-hydroxylamine 30 ml of nitric acid with a density of 1.49 were added over two hours at not more than 0° C. to a solution of 30 g of m-fluoro-toluene and 60 ml of 36° Be sulfuric acid cooled to −15° C. and the mixture was stirred at 0° C. for one hour and poured over ice. The mixture was extracted with methylene chloride and the organic phase was washed with water, dried and evaporated to dryness under reduced pressure. The residue was triturated with isopropyl ether and was filtered and the product was dried to obtain 21.8 g of 3-fluoro-4,6-dinitro-toluene melting at 76° C. The latter was reacted as in Example 1 to obtain 0-(2,4-dinitro-5-methyl-phenyl)-hydroxylamine melting at 105° C.

EXAMPLE 14

0-[4-nitro-2-(1RS-hydroxyethyl)-phenyl]-hydroxylamine 23.7 g of 2-fluoro-acetophenone were added to 0° to 10° C. to 113 ml of nitric acid with a density of 1.52 and after standing for 30 minutes at −10° to 0° C., the mixture was poured into an ice water mixture. The mixture was filtered and the product was washed with water and dried to obtain 26.98 g of 2-fluoro-5-nitro-acetophenone melting at 56°–58° C.

1.04 g of sodium borohydride were added at 0° to 5° C. to a solution of 10 g of the above product in 100 ml of methanol and the mixture was held at 0° to 5° C. for one hour and was then poured into ice. The mixture was extracted with dichloromethane and the organic phase was dried and evaporated to dryness under reduced pressure to obtain 9.47 g of 1-(2-fluoro-5-nitro-phenyl)- ethanol melting at less than 50° C. The latter was reacted as in Example 1 to obtain 0-[4-nitro-2-(1RS-hydroxyethyl)-phenyl]-phenyl]-hydroxylamine melting at 120° C.

EXAMPLE 15

0-(4-nitro-2-ethoxycarbonyl-phenyl)-hydroxylamine

A mixture of 35 g of 2-fluoro-benzoyl chloride and 400 ml of ethanol was stirred for three hours and was allowed to stand overnight. The mixture was distilled to dryness at 50° C. and 30–40 mm Hg and the residue was taken up in methylene chloride The solution was washed with 5% aqueous sodium bicarbonate and then with water, dried and evaporated to dryness under reduced pressure. The product was rectified at 14 mm Hg to obtain 34 g of ethyl 2-fluoro-benzoate with a boiling point of 90°–91° C. at 14 mm Hg.

31.8 g of the said product were added with cooling to 60 ml of concentrated sulfuric acid and 15.9 g of nitric acid with a density of 1.5 were added with stirring at 0° to 5° C. over 30 minutes to the mixture. The mixture was stirred for 2 hours at 5° to 10° C. and was poured into ice-water. The mixture was extracted with methylene chloride and the combined organic phases were washed with 5% aqueous sodium bicarbonate solution, with water, dried and evaporated to dryness under reduced pressure. The residue was triturated with hexane, filtered and the product dried under reduced pressure to obtain 37.7 g of ethyl 2-fluoro-5-nitro-benzoate melting at 53°–54° C. The latter was reacted as in Example 1 to obtain 0-(4-nitro-2-ethoxycarbonyl-phenyl)-hydroxylamine melting at 116°–117° C.

EXAMPLE 16

0-(4-nitro-2-diethylcarbamoyl-phenyl)-hydroxylamine

A solution of 42 g of 2-fluoro-5-nitro-benzoic acid [prepared by Chim. et Ind. 1970, p. 892] melting at 139°–140° C. and 120 ml of thienyl chloride was refluxed for two hours and was then distilled at 40° C. under a pressure of 30 to 40 mm Hg. The residue was taken up in benzene and the solution was evaporated to dryness to obtain 44 g of 2-fluoro-5-nitro-benzoyl chloride melting at 59°–60° C.

A solution of 40.7 g of the said product in 100 ml of benzene was added over 30 minutes with stirring at 5° C. to a mixture of 32 g of diethylamine and 350 ml of anhydrous benzene and the mixture was stirred at 20° C. for one hour and was filtered. The filter was washed with benzene and the filtrate was washed with hydrochloric acid, with 10% aqueous sodium bicarbonate and then with water. The organic phase was dried, treated with activated carbon, filtered and evaporated to dryness under reduced pressure at 50° C. The 38 g of residue were chromatographed over silica gel and eluted with a 9-1 methylene chloride-ethyl acetate mixture to obtain 33 g of N,N-diethyl-2-fluoro-5-nitro-benzamide with a refractive index of $n_D^{34} = 1.5330$. The said product was reacted as in Example 1 to obtain 0-(4-nitro-2-diethylcarbamoyl-phenyl)-hydroxylamine melting at 139°–140° C.

EXAMPLE 17

0-(4-nitro-naphth-1-yl)-hydroxylamine 1-fluoro-naphthalene was reacted to obtain 1-fluoro-4-nitro-naphthalene with a melting point of 75°–76° C. which was then reacted as in Example 1 to obtain 0-(4-nitro-naphth-1-yl)-hydroxylamine melting at 108°–110° C.

EXAMPLE 18

0-(4-nitro-2-methoxycarbonyl-phenyl)-hydroxylamine

A solution of 20 g of 2-fluoro-5-nitro-benzoic acid in 60 ml of thionyl chloride was refluxed for one hour and was then evaporated to dryness under reduced pressure. The residue was taken up in 50 ml of benzene and the solution was distilled to dryness under reduced pressure. This procedure was repeated several times and the reacting acid chloride was added to 400 ml of methanol. The solution was stirred for two hours at 25°–30° C. and stood overnight and then distilled to dryness under reduced pressure at 50° C. The residue was taken up in isopropyl ether and the solution was washed with water, dried and evaporated to dryness under reduced pressure to obtain 13 g of methyl 2-fluoro-5-nitro-benzoate melting at 52°–53° C. The said product was reacted as in Example 1 to obtain 0-(4-nitro-2-methoxycarbonyl-phenyl)-hydroxylamine melting at 175°~180° C.

EXAMPLE 19

0-(4-nitro-3-acetamido-phenyl)-hydroxylamine 1-fluoro-3-acetamido-benzene was reacted to obtain 1-fluoro-3-acetamido-4-benzene melting at 40° C. which was reacted as in Example 1 to obtain 0-(4-nitro-3-acetamido-phenyl)-hydroxylamine melting at 150°–152° C.

EXAMPLE 20

0-(4-nitro-3-amino-phenyl)-hydroxylamine

A solution of 20 g of 3-fluoro-6-nitro-acetanilide in 200 ml of 6N hydrochloric acid was heated at 110° to 120° C. for 30 minutes and the mixture was poured into ice and water. The mixture was filtered and the solid product was crystallized from isopropyl ether to obtain 7.5 g of 3-fluoro-6-nitro-aniline melting at 99° C. The said product was reacted as in Example 1 to obtain 0-(4-nitro-3-amino-phenyl)-hydroxylamine melting at 190°–191° C.

EXAMPLE 21

0-(4-ethoxycarbonyl-2-nitro-phenyl)-hydroxylamine 2 ml of concentrated sulfuric acid were added to a solution of 10 g of 3-nitro-4-fluoro-benzoic acid in 50 ml of ethanol and the mixture was refluxed for three hours. 8 ml of concentrated sulfuric acid were added to the mixture which was refluxed for 16 hours and was cooled to 20° C. The mixture was poured into water with stirring and was filtered. The solid product was washed and dried to obtain 10.5 g of ethyl 3-nitro-4-fluoro-benzoate melting at 50° C. The said product was reacted as in Example 1 to obtain 0-(4-ethoxycarbonyl-2-nitro-phenyl)-hydroxylamine melting at 102° C.

EXAMPLE 22

0-(4-nitro-3-n-pentyloxy-phenyl)-hydroxylamine 3-fluoro-phenol was etherified to obtain 3-fluoro-n-pentyloxy-benzene with a refractive index of $n_D^{33} = 1.4741$ which was reacted to obtain 2-(n-pentyloxy)-4-fluoro-nitro benzene which was reacted as in Example 1 to obtain 0-(4-nitro-3-n-pentyloxyphenyl)-hydroxylamine melting at 78°–79° C.

EXAMPLE 23

0-(4-nitro-3-allyloxy-phenyl)-hydroxylamine 3-fluoro-phenol was reacted with allyl bromide to form 3-fluoro-allyloxy-benzene with a refractive index of $n_D^{23} = 1.4985$ which was reacted with nitric acid to obtain 2-allyloxy-4-fluoro-nitro-benzene with a refractive index of $n_D^{23} = 1.5432$ which was reacted as in Example 1 to obtain 0-(4-nitro-3-allyloxy-phenyl)-hydroxylamine melting at 94°–95° C.

EXAMPLE 24

0-(4-nitro-3-isopropoxy-phenyl)-hydroxylamine 3-fluoro-phenol and isopropyl iodide were reacted to form 3-fluoro-isopropoxy-benzene which was reacted with nitric acid to obtain 2-isopropoxy-4-fluoro-nitro benzene which was reacted as in Example 1 to obtain 0-(4-nitro-3-isopropoxy-phenyl)-hydroxylamine melting at 104° C.

EXAMPLE 25

0-(4-nitro-3-ethoxy-phenyl)-hydroxylamine 3-fluoro-phenol and ethyl iodide were reacted to form 3-fluoro-ethoxy benzene with a refractive index of $n_D^{25} = 1.4823$ which was reacted with nitric acid to obtain 2-ethoxy-4-fluoronitro benzene with a melting point of 28°~30° C. which was reacted to obtain 0-(4-nitro-3-ethoxy-phenyl)-hydroxylamine melting at 97°~98° C.

EXAMPLE 26

0-(4-nitro-3-n-butoxy-phenyl)-hydroxylamine 3-fluoro-phenyl and n-butyl iodide were reacted to form 3-fluoro-n-butoxy benzene with a refractive index of $n_D^{20} = 1.4762$ which was nitrated to form 2-n-butoxy-4-fluoro-nitro benzene with a refractive index of $n_D^{26} = 1.5180$ which was reacted as in Example 1 to obtain 0-(4-nitro-3-n-butoxy-phenyl)-hydroxylamine with a melting point of 75°~76° C.

EXAMPLE 27

0-(4-acetyl-2-nitro-phenyl)-hydroxylamine 1-fluoro-4-acetyl-benzene was reacted with nitric acid to obtain 2-fluoro-5-acetyl-nitro benzene with a melting point of 56°–58° C. which was reacted as in Example 1 to obtain 0-(4-acetyl-2-nitro-phenyl)-hydroxylamine melting at 132° C.

EXAMPLE 28

0-[4-nitro-3-(1RS-hydroxy-ethyl)-phenyl]-hydroxylamine m-fluoroacetophenone was reacted with nitric acid to form 4-fluoro-3-nitro-acetophenone which was reduced with sodium borohydride to obtain 4-nitro-3-(1RS-hydroxy ethyl)-fluorobenzene which was reacted as in Example 1 to obtain 0-[4-nitro-3-(1RS-hydroxy-ethyl)-phenyl]-hydroxylamine melting at 118°–120° C.

EXAMPLE 29

0-[4-nitro-3-(3,3-dichloroallyloxy)-phenyl]-hydroxylamine 3-fluoro-phenol and 3,3-dichloro-allyl chloride were reacted in the presence of a base to obtain 4-nitro-3-(3,3-dichloroallyloxy)-fluorobenzene which was reacted as in Example 1 to obtain 0-[4-nitro-3-(3,3-dichloroallyloxy)-phenyl]-hydroxylamine melting 96°–98° C.

EXAMPLE 30

0-(4-nitro-3-methylamino-phenyl)-hydroxylamine 2-acetamido-fluorobenzene was reacted with nitric acid to form 4-nitro-3-acetamido-fluorobenzene, removing the acetyl group and methylating the latter to form 4-nitro-3-methylamino-fluorobenzene which was reacted as in Example 1 to obtain 0-(4-nitro-3-methylamino-phenyl)-hydroxylamine melting at 157°–158° C.

EXAMPLE 31

0-(4-nitro-3-dimethylamino-phenyl)-hydroxylamine 4-nitro-3-dimethylamino-fluoro benzene prepared as in Example 30 was reacted as in Example 1 to obtain 0-(4-nitro-3-dimethylamino-phenyl)-hydroxylamine melting at 73° C.

EXAMPLE 32

0-[4-nitro-3-(4-nitrophenoxy)-phenyl]-hydroxylamine p-chloro-nitrobenzene and m-fluoro-phenol in tetrahydrofuran in the presence of sodium hydride were reacted to obtain 3-(4-nitrophenoxy)-fluorobenzene which was nitrated to form 4-nitro-3-(4-nitrophenoxy)-fluorobenzene which was reacted as in Example 1 to obtain 0-[4-nitro-3-(4-nitrophenoxy)-phenyl]-hydroxylamine melting at 132° C.

EXAMPLE 33

0-(4-nitro-2-trifluoromethyl-phenyl)-hydroxylamine

STEP A:

N-(4-nitro-2-trifluoromethyl-phenoxy)-phthalimide 11.5 g of sodium hydride as a 50% oil suspension were admixed at 20° C. with 300 ml of anhydrous diemthylformamide and after cooling the mixture to 5° to 10° C., 36.5 g of N-hydroxy-phthalimide were added thereto. The mixture was stirred at 20° C. for 30 minutes and 50 g of 4-nitro-2-trifluoromethyl-chloro benzene were added over 10 minutes. The suspension was heated at 80°–85° C. for one hour and was cooled to 20° C. and poured over ice. The mixture was stirred for one hour and was filtered. The solid product was washed with water and dried to obtain 60.7 g of N-(4-nitro-2-trifluoromethyl-phenoxy)-phthalimide melting at 190° C.

STEP B:

0-(4-nitro-2-trifluoromethyl-phenyl)-hydroxylamine 2 ml of hydrated hydrazine were added to a solution of 5 g of the product of Step A in 50 ml of ethanol and the mixture was stirred for 90 minutes at 20° C. and was poured over ice. The mixture was adjusted to a pH of 1 by addition of hydrochloric acid and was filtered. The filter was washed with methylene chloride and the decanted aqueous filtrate was extracted with methylene chloride. The combined organic phases were washed with water dried and evaporated to dryness under reduced pressure. The residue was chromatographed over silica gel and eluted with methylene chloride. The product was triturated with hot hexane which was then cooled and filtered. The product was washed with hexame and dried at 40° C. under reduced pressure to obtain 2.1 g of 0-(4-nitro-2-trifluoromethyl-phenyl)-hydroxylamine melting at 106° C.

EXAMPLE 34

0-(8-nitro-5-quinolyl)-hydroxylamine

A mixture of 25.2 g of 3-chloro-6-nitro-aniline, 21 g of arsenic acid and 35.1 ml of glycerine was heated to reflux and after cooling the mixture to 20°~30° C., 25.5 ml of 66° Be sulfuric acid were added thereto. The mixture was heated at 140° C. for 8 hours and was poured over ice. The mixture was filtered and the solid product was dissolved in methylene chloride. The solution was neutralized and extracted with methylene chloride. The combined organic phases were dried, treated with activated carbon, filtered and evaporated to dryness under reduced pressure. The 10 g of residue were chromatographed over silica gel and eluted with methylene chloride to obtain 8.61 g of 5-chloro-8-nitro-quinoline melting at 136°-138° C. which was reacted with N-hydroxyphthalimide to obtain 0-(8-nitro-5-quinolyl)-phthalimide melting at 226°-228° C. The latter was reacted to obtain 0-(8-nitro-5-quinolyl)-hydroxylamine melting at 186°-188° C.

EXAMPLE 35

0-(4-nitro-3-trifluoromethyl-phenyl)-hydroxylamine

N-hydroxy-phthalimide and 2-trifluoromethyl-4-chloro-nitrobenzene were reacted to obtain 0-(3-trifluoromethyl-4-nitro-phenoxy)-phthalimide melting at 145° C. which was reacted to obtain 0-(4-nitro-3-trifluoromethyl-phenyl)-hydroxylamine melting at 44° C.

EXAMPLE 36

0-(7-chloro-4-quinolyl)-hydroxylamine

N-hydroxy-phthalimide and 4,7-dichloro-quinoline were reacted to form 0-(7-chloro-4-quinolyl)-phthalimide melting at 225° C. and the latter is reacted to obtain 0-(7-chloro-4- quinolyl)-hydroxylamine melting at 175° C.

EXAMPLE 37

0-(5-nitro-6-quinolyl)-hydroxylamine

N-hydroxy-phthalimide and 5-nitro-6-chloro-quinoline were reacted to form 0-(5-nitro-6-quinolyl)-phthalimide melting at 185° C. which was reacted to obtain 0-(5-nitro-6-quinolyl)hydroxylamine melting at 165° C.

EXAMPLE 38

0-(4-nitrobenzyl)-hydroxylamine hydrochloride

N-hydroxy-phthalimide and 4-nitro benzyl chloride were reacted to obtain 0-(4-nitro-benzyloxy)-phthalimide melting at 194°-195° C. which was reacted to obtain 0-(4-nitrobenzyl)hydroxylamine hydrochloride melting at 209°-211° C.

EXAMPLE 39

0-(2-nitrophenyl)-hydroxylamine

N-hydroxyphthalimide and 2-chloro-nitrobenzene were reacted to obtain 0-(2-nitro-phenoxy)-phthalimide melting at 251°-252° C. which was reacted to obtain 0-(2-nitrophenyl)-hydroxylamine melting at 163°-164° C.

EXAMPLE 40

0-(4-cyano-2-nitro-phenyl)-hydroxylamine 4-chloro-benzonitrile was reacted with nitric acid to obtain 3-nitro-4-chloro-benzonitrile melting at 100°-101° C. which was reacted with N-hydroxy-phthalimide to obtain 0-(4-cyano-2-nitrophenoxy)-phthalimide melting at 233°-234° C. The latter was reacted to obtain 0-(4-cyano-2-nitro-phenyl)-hydroxylamine melting at 154°-155° C.

EXAMPLE 41

0-(4-methylsulfonyl-2-nitro-phenyl)-hydroxylamine 4-methylsulfonyl-bromobenzene was reacted with nitric acid to obtain 2-nitro-4-methylsulfonyl-bromobenzene melting at 126° C. which was reacted with N-hydroxy-phthalimide to obtain 0-(4-methylsulfonyl-2-nitro-phenoxy)-phthalimide melting at 215° C. The latter was reacted to obtain 0-(4-methylsulfonyl-2-nitro-phenyl)-hydroxylamine melting at 190° C.

EXAMPLE 42

0-(4-nitro-2-isopropyl-phenyl)-hydroxylamine

STEP A: 2-isopropyl-acetanilide 86 g of acetic acid anhydride were added to a solution of 108 g of 2-isopropyl-aniline and 250 ml of benzene and another 86 g of acetic acid anhydride were added thereto. The mixture was stirred at 20° C. for 16 hours and was washed with water, with aqueous sodium bicarbonate, with water, dried and evaporated to dryness under reduced pressure. The residue was triturated with hexane, cooled and filtered. The product was washed with hexane and dried under reduced pressure to obtain 115 g of 2-isopropylacetanilide melting at 67°-68° C.

STEP B: 2-isopropyl-4-nitro-acetanilide 32 ml of nitric acid with a density of 1.50 were added at −5° to −10° C. to a solution of 71 g of the product of Step A, 300 ml of acetic acid anhydride and 100 ml of acetic acid and the mixture was stirred at −5° C. for 30 minutes and at 0° to 2° C. for three hours and was poured into ice-water. The mixture was stirred for one hour and was filtered and the product was washed with water and dried. The 70 g of product were chromatographed over silica gel and eluted with a 7-3 methylene chloride-ethyl acetate mixture to obtain 19.4 g of 2-isopropyl-4-nitro-acetanilide melting at 160°-161° C.

STEP C: 2-isopropyl-4-nitro-aniline

A solution of 19 g of the product of Step B and 60 ml of 8N hydrochloric acid was refluxed for 2 hours and then was cooled and filtered. The product was suspended in water and the suspension was made alkaline by addition of 10% aqueous sodium carbonate solution. The mixture was extracted with isopropyl ether and the hydrochloric acid mother liquors were diluted with water, made alkaline and extracted with isopropyl ether. The combined organic phases were washed with water, dried and evaporated to dryness under reduced pressure to obtain 11.7 g of 2-isopropyl-4-nitro-aniline.

STEP D: 3-isopropyl-4-bromo-nitrobenzene

A solution of 7.5 g of sodium nitrite in 20 ml of water was added at −20° C. to 0° C. over 20 minutes to a suspension of 18.5 g of the product of Step C, 120 ml of a 48% hydrobromic acid solution and 80 ml of water and the mixture was stirred at 0° C. for 15 minutes and kept thereafter at 0° C. A solution of 22 g of cuprous bromide in 80 ml of 48% hydrobromic acid solution was heated with stirring to 50°-55° C. and the previous solution was then added thereto. The mixture was stirred at 55°-60° C. for one hour, was cooled and poured into water. The mixture was extracted with methylene chloride and the combined organic phases were washed with N sodium hydroxide solution, with water, dried and evaporated to dryness under reduced pressure at 50° C. The residue was rectified under reduced pressure to obtain 20.4 g of 3-isopropyl-4-bromo-nitrobenzene with a boiling point of 150°–152° C. at 8 mm Hg and having a refractive index of $n_D^{22}=1.5775$.

STEP E: 0-(4-nitro-2-isopropyl-phenyl)-hydroxylamine

The product of Step D was reacted with N-hydroxyphthalimide to obtain 0-(4-nitro-2-isopropyl-phenoxy)-phthalimide melting at 125°–126° C. which was reacted to obtain 0-(4-nitro-2-isopropyl-phenyl)-hydroxylamine melting at 81°~82° C.

EXAMPLE 43

0-(4-fluoro-2-nitro-phenyl)-hydroxylamine

STEP A: 2-nitro-4-fluoro-acetanilide 6.5 ml of nitric acid with a density of 1.42 were added at 0° to 5° C. over 30 minutes to a solution of 13.8 g of 4-fluoro-acetanilide [process of Acta Chemica Scand., 1976, p. 141] in 35 ml of concentrated sulfuric acid and the mixture was stirred at 0° to 5° C. for two hours. 10 ml of acetic acid anhydride were added to the mixture which was stirred at 0° C. for one hour and was then poured into ice-water. The mixture was filtered and the solid product was washed and dried to obtain 14 g of 2-nitro-4-fluoro-acetanilide melting at 70°–71° C.

STEP B: 2-nitro-4-fluoro-aniline

A mixture of 40 g of the product of Step A in 100 ml of 8N hydrochloric acid was refluxed with stirring for one hour during which crystallization occured and the mixture was cooled to 20° C. and iced for one hour. The mixture was filtered and the solid product was washed with water until the wash water was neutral and dried under reduced pressure to obtain 32.2 g of residue melting at 94°~95° C. The latter was suspended in 500 ml of methylene chloride and 300 ml of N sodium hydroxide solution were added thereto with stirring. The decanted organic phase was washed with water, dried and evaporated to dryness under reduced pressure to obtain 27.2 g of 2-nitro-4-fluoro-aniline melting at 94°–95° C.

STEP C: 2-nitro-4-fluoro-bromobenzene

A solution of 10 g of sodium nitrite in 30 ml of water were added with stirring at 0° C. to a suspension of 21.6 g of the product of Step B, 69 ml of 48% hydrobromic acid and 138 ml of water and the mixture was stirred at 0° C. for 10 minutes and then added with stirring to a solution of 30 g of cuprous bromide in 105 ml of 48% hydrobromic acid at 60° C. The mixture was stirred at 55°–60° C. for one hour and was poured into ice water. The mixture was extracted with isopropyl ether and the combined organic phases were dried and evaporated to dryness under reduced pressure. The residue was chromatographed over silica gel and eluted with methylene chloride. The solution was evaporated to dryness and the residue was dried under reduced pressure to obtain 20.2 g of 2-nitro-4-fluoro-bromobenzene melting at 40°–41° C.

STEP D: 0-(4-fluoro-2-nitro-phenyl)-hydroxylamine

N-hydroxyl-phthalimide and the product of Step C were reacted to form 0-(4-fluoro-2-nitro-phenoxy)-phthalimide melting at 181°–182° C. which was reacted to form 0-(4-fluoro-2-nitrophenyl)-hydroxylamine melting at 87°–88° C.

EXAMPLE 44

0-(8-chloro-4-quinolyl)-hydroxylamine

N-hydroxy-phthalimide and 4-bromo-8-chloroquinoline (a known compound) were reacted to obtain 0-(8-chloro-4-quinolyl)-phthalimide which was reacted to obtain 0-(8-chloro-4-quinolyl)-hydroxylamine melting at 194° C.

EXAMPLE 45

0-(8-trifluoromethyl-4-quinolyl)-hydroxylamine

N-hydroxy-phthalimide and 4-bromo-8-trifluoromethylquinoline (a known compound) were reacted to obtain 0-(8-trifluoromethyl-4-quinolyl)-phthalimide which was reacted to obtain 0-(8-trifluoromethyl-4-quinolyl)-hydroxylamine melting at 152° C.

EXAMPLE 46

0-(4-nitro-3-ethyl-phenyl)-hydroxylamine 3-ethyl-fluorobenzene was reacted with nitric acid to obtain 4-nitro-3-ethyl-fluorobenzene which was reacted with N-hydroxy-phthalimide to form 0-(4-nitro-3-ethyl-phenoxy)-phthalimide which was reacted to form 0-(4-nitro-3-ethylphenyl)-hydroxylamine melting at 55°–56° C.

EXAMPLE 47

0-[4-nitro-3-(phenylsulfonylmethyl)-phenyl]-hydroxylamine 4-nitro-fluorobenzene and phenylsulfonylmethyl chloride were reacted in dimethylsulfoxide in the presence of potassium tert.-butylate to form 4-nitro-3-(phenylsulfonylmethyl)-fluorobenzene which was reacted with N-hydroxy-phthalimide to form 0-[4-nitro-3-(phenylsulfonylmethyl)-phenoxy]-phthalimide which was reacted to obtain 0-[4-nitro-3-phenylsulfonylmethyl)-phenyl]-hydroxylamine melting at 195°–196° C.

EXAMPLE 48

0-(3-trifluoromethyl-phenyl)-hydroxylamine hydrochloride

A mixture of 33.6 g of potassium hydroxide, 100 ml of 3-trifluoromethyl-phenol, 420 ml of water and 200 ml of methyl cyclohexane was heated to reflux and heating was stopped while a freshly prepared solution of 17 g of hydroxylamine-0-sulfonic acid in 40 ml of water was added thereto. The mixture was refluxed for 10 minutes and cooled to 20° C. The decanted aqueous phase was extracted with ether and the combined organic phases were washed with water, with N sodium hydroxide solution, with water and dried. The solution was acidified with an ethanolic solution of gaseous hydrogen chloride and was filtered. The product was washed with ether and dried under reduced pressure to obtain 6 g of 0-(3-trifluoromethyl-phenyl)-hydroxylamine hydrochloride melting at 160°–162° C.

EXAMPLE 49

0-(4-ethoxycarbonyl-phenyl)-hydroxylamine hydrochloride

Hydroxylamino-0-sulfonic acid and 4-ethoxycarbonylphenol were reacted to obtain 0-(4-ethoxycarbonyl-phenyl)-hydroxylamine hydrochloride melting at 135° C.

EXAMPLE 50

0-(4-tert.-butyl-phenyl)-hydroxylamine hydrochloride

Using the procedure of Example 48, hydroxylamine-0-sulfonic acid and 4-tert.-butyl phenol were reacted to obtain 0-(4-tert.-butyl-phenyl)-hydroxylamine hydrochloride melting at 140° C.

EXAMPLE 51

0-(2,4-dichloro-phenyl)-hydroxylamine

Hydroxylamine-0-sulfonic acid and 2,4-dichloro-phenol were reacted to obtain 0-(2,4-dichloro-phenyl)-hydroxylamine melting at 79°–80° C.

EXAMPLE 52

0-(4-fluoro-phenyl)-hydroxylamine hydrochloride

Hydroxylamine-0-sulfonic acid and 4-fluoro-phenol were reacted to obtain 0-(4-fluoro-phenyl)-hydroxylamine hydrochloride melting at 144°–146° C. (decomposition).

EXAMPLE 53

0-(4-dimethylcarbamoyl-phenyl)-hydroxylamine 4-acetyloxy-benzoic acid was reacted with thionyl chloride to obtain 4-acetyloxy-benzoyl acid chloride which was reacted with dimethylamine to obtain N,N-dimethyl-4-acetyloxy-benzcarboxamide which was hydrolyzed to obtain 4-dimethylcarbamoylphenol melting at 160°–161° C. The latter was reacted with hydroxylamine-0-sulfonic acid to obtain 0-(4-dimethylcarbamoyl-phenyl)-hydroxylamine melting at 103°–104° C.

EXAMPLE 54

0-(4-chloro-3-methyl-phenyl)-hydroxylamine hydrochloride

Hydroxylamine-0-sulfonic acid and 3-methyl-4-chlorophenol were reacted to obtain 0-(4-chloro-3-methyl-phenyl)-hydroxylamine hydrochloride melting at 154°–156° C.

EXAMPLE 55

0-(4-chloro-2-methyl-phenyl)-hydroxylamine hydrochloride

Hydroxylamine-0-sulfonic acid and 2-methyl-4-chlorophenol were reacted to obtain 0-(4-chloro-2-methyl-phenyl)-hydroxylamine hydrochloride melting at 130°–132° C.

EXAMPLE 56

0-(4-cyano-phenyl)-hydroxylamine

Hydroxylamine-0-sulfonic acid and 4-cyano-phenol were reacted to obtain 0-(4-cyano-phenyl)-hydroxylamine melting at 110° C.

EXAMPLE 57

0-(3-chlorophenyl)-hydroxylamine hydrochloride 3-chloro-phenol and hydroxylamine-0-sulfonic acid were reacted to obtain 0-(3-chlorophenyl)-hydroxylamine hydrochloride melting at 155° C.

EXAMPLE 58

0-(3-nitrophenyl)-hydroxylamine 3-nitro-phenol and hydroxylamine-0-sulfonic acid were reacted to form 0-(3-nitrophenyl)-hydroxylamine with a melting point of 56° C.

EXAMPLE 59

0-(4-acetylphenyl)-hydroxylamine 4-acetylphenol and hydroxylamine-0-sulfonic acid were reacted to obtain 0-(4-acetylphenyl)-hydroxylamine melting at 118° C.

EXAMPLE 60

0-(3,4-dichloro-phenyl)-hydroxylamine hydrochloride 3,4-dichloro-phenol and hydroxylamine-0-sulfonic acid were reacted to obtain 0-(3,4-dichloro-phenyl)-hydroxylamine hydrochloride melting at 175° C.

EXAMPLE 61

0-[4-nitro-3-(methylsulfonylmethyl)-phenyl]-hydroxylamine 4-nitro-3-(methylsulfonylmethyl)-phenol and hydroxylamine-0-sulfonic acid are reacted to obtain 0-[4-nitro-3-(methylsulfonylmethyl)-phenyl]-hydroxylamine.

EXAMPLE 62

4-nitro-3-cyanomethyl-phenol and hydroxylamine-0-sulfonic acid are reacted to obtain 0-[4-nitro-3-(methylsulfonylmethyl)-phenyl]-hydroxylamine.

EXAMPLE 63

0-[3-propyn-2-yloxy)-4-nitro-phenyl]-hydroxylamine 3-fluoro-phenol and propargyl bromide were reacted to form 2-(prop-1-yn-3-yloxy)-3-fluoro benzene with a boiling point of 95°–96° C. at 20 mm Hg which was then reacted with nitric acid to obtain 2-(prop-1-yn-3-yloxy)-4-fluoro-nitrobenzene melting at 38°–39° C. A solution of 19.5 g of the said product in 150 ml of ethanol and 50 ml of water and 8.4 g of hydroxylamine hydrochloride was cooled to 5° C. with stirring and 22 ml of 10N sodium hydroxide solution were added thereto at 5° to 10° C. over 30 minutes. The mixture was stirred at 20° C. for 16 hours and was poured into water. The stirred mixture was cooled to 5° C. and was filtered. The product was washed and dried under reduced pressure to obtain 15 g of product melting at 95°–96° C. The product was crystallized from methanol to obtain 8 g of 0-[3-(propyn-2-yloxy)-4-nitro-phenyl]-hydroxylamine melting at 99°–100° C.

EXAMPLE 64

An emulsifiable concentrate was prepared containing, by weight, 15% of the product of Example, 6.4% of Atlox 4851 (oxyethylenated triglyceride combined with a sulfonate, acid index of 1.5), 3.2% of Atlox 4855 (oxyethylenated triglyceride combined with a sulfonate, acid index of 3) and 75.4% of xylene.

A wettable powder was prepared containing 25% of the product of Example 2, 15% of Ekapersol (condensation product of sodium naphthalene sulfonate), 35% of Zeosil 39 (synthetic hydrated silica obtained by precipitation) and 25% of Vercoryl S (colloidal kaolin).

PHARMACOLOGICAL DATA

A. Study of the "Warburg" effect

The products of the invention possess the property of diminishing the inhibiting effect of oxygen on photosynthesis (Warburg effect) which results in a stimulation of the photosynthesis and an increase in the yield of the harvest. The test is carried out on corn leaf cuttings which are floated either on distilled water or on a solution of the product being studied (10 mmoles per liter). The leaves were placed in water tight glass chambers under illumination of 300 W/m$^2$, the temperature of which was regulated at 25° C. The air in the chamber was continually renewed either with normal air (21% $O_2$–350 ppm $CO_2$), or with pure oxygen (nearly 100%). When steady photosynthesis was reached 0.09μ mole of $^{14}CO_2$ was introduced (specific activity: 22 mCi/mM) and the leaves were left for 15 minutes in the light and in the presence of radio-active carbon gas.

The leaves were then immersed in liquid nitrogen and kept and they were subsequently burned to determine the amount of $^{14}CO_2$ fixed by photosynthesis. The results were expressed as a comparison between the radio-activity fixed by the control leaves and by those treated with the products being studied. The leaves were treated with 10μ moles of certain products of the examples and were placed in an atmosphere containing 100% of $O_2$. The results obtained on the inhibition of oxygen vis-a-vis photosynthesis are in the following table.

TABLE I

| Product of Example | Photosynthesis in % of untreated control leaves (100) |
| --- | --- |
| 1 | 165 (±15) |
| 2 | 140 (±13) |
| 3 | 138 (±12) |
| 4 | 145 (±10) |
| 5 | 125 (±9) |
| 33 | 140 (±11) |
| 51 | 152 (±12) |

TABLE I-continued

| Product of Example | Photosynthesis in % of untreated control leaves (100) |
| --- | --- |
| 57 | 160 (±14) |

The table expresses the percentage of photosynthesis of corn leaves measured by absorption of $CO_2$ in comparison with the untreated control leaves in the presence of an atmosphere containing 100% of oxygen (the inhibition of photosynthesis of $O_2$ is from 30 to 50% in these tests).

B. Study of the activity of the products of examples 1 and 2 as growth factors The test was carried out on a crop of tomatoes of Europcel variety using a Fisher block with 5 repetitions. The elementary plots were 20 m$^2$ (10×2 m) and an untreated control plant was included in each repetition. The test was carried out on clayey, calcareous, alluvial soil and the treatments were carried out with an appliance secured on the back, of van der Weilj type, on the basis on 750 l./ha, at a constant pressure of 3 bars. The treatments were effected either after the petals of the first flowers had fallen ($T_1$), or after the petals of the last flowers had fallen ($T_2=T_1+20$ days) or at the setting, that is to say when the fruits are just forming. The products of examples 1 and 2 were used at quantities of 40, 60 or 120 g/ha three times or once and two tomato harvests were realized. At each harvaest, the yield in kg per 32 tomato plants was determined as compared with an untreated control plant. In this test, it was found that the products of examples 1 and 2 present a useful growth factor activity.

Various modifications of the products and process of the invention may be made without departing from the spirit or scope thereof and it is to be understood that the invention is intended to be limited only as defined in the appended claims.

What is claim is:

1. A compound selected from the group consisting of 0-(5-nitro-8-quinolyl)-hydroxylamine and their non-toxic, pharmaceutically acceptable acid addition salts.

* * * * *